(12) United States Patent
Tang et al.

(10) Patent No.: US 11,179,139 B2
(45) Date of Patent: *Nov. 23, 2021

(54) TENSION TRANSMISSION DEVICE AND THREE-DIMENSIONAL MECHANICAL PROBE USING SAME

(71) Applicant: Shenzhen Mindray Bio-Medical Electronics Co., Ltd., Shenzhen (CN)

(72) Inventors: Ming Tang, Shenzhen (CN); Zhen-Yu Chen, Shenzhen (CN); Le-Yun Bai, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 324 days.

This patent is subject to a terminal disclaimer.

(21) Appl. No.: 16/518,782

(22) Filed: Jul. 22, 2019

(65) Prior Publication Data

US 2019/0336102 A1 Nov. 7, 2019

Related U.S. Application Data

(63) Continuation of application No. 14/972,388, filed on Dec. 17, 2015, now Pat. No. 10,398,410, which is a (Continued)

(30) Foreign Application Priority Data

Jun. 19, 2013 (CN) .......................... 201310244524.0

(51) Int. Cl.
*A61B 8/00* (2006.01)
*A61B 8/08* (2006.01)
*A61B 8/12* (2006.01)

(52) U.S. Cl.
CPC .............. *A61B 8/4466* (2013.01); *A61B 8/08* (2013.01); *A61B 8/12* (2013.01); *A61B 2576/00* (2013.01)

(58) Field of Classification Search
CPC ........... A61B 8/4466; A61B 8/08; A61B 8/12; A61B 2576/00
See application file for complete search history.

(56) References Cited

U.S. PATENT DOCUMENTS 4,688,555 A * 8/1987 Wardle ................ A61B 1/0052
600/149
5,048,529 A * 9/1991 Blumenthal ......... G10K 11/355
600/446
(Continued)

FOREIGN PATENT DOCUMENTS

CN 1720006 A 1/2006
CN 1791362 A 6/2006
(Continued)

*Primary Examiner* — Bo Joseph Peng
(74) *Attorney, Agent, or Firm* — Kory D. Christensen

(57) ABSTRACT

A tension transmission device as a control system for a probing portion of a three-dimensional mechanical probe is fitted to a support portion. The tension transmission device includes a driving shaft, a first tension member, and a second tension member. The driving shaft defines first and second fastening points. The first fastening point and the second fastening point are located at axially-distanced points of the driving shaft which are not diametrically opposite. The first and second tension members wind around a circumference of the driving shaft guided by a first pulley and a second pulley, to rotate and manipulate the driven shaft of the probing portion.

13 Claims, 12 Drawing Sheets

Related U.S. Application Data continuation of application No. PCT/CN2014/074198, filed on Mar. 27, 2014.

(56) References Cited

U.S. PATENT DOCUMENTS

| | | | |
|---|---|---|---|
| 5,167,221 A | | 12/1992 | Chikama |
| 5,255,684 A | * | 10/1993 | Rello ........................ A61B 8/12 600/437 |
| 5,351,692 A | * | 10/1994 | Dow ........................ A61B 8/12 600/445 |
| 5,450,851 A | * | 9/1995 | Hancock ................... A61B 8/12 600/446 |
| 8,021,304 B2 | * | 9/2011 | Kadokura ............ A61B 8/4461 600/459 |
| 2008/0161694 A1 | | 7/2008 | Kim |
| 2008/0287801 A1 | * | 11/2008 | Magnin ................ A61B 8/4461 600/463 |

FOREIGN PATENT DOCUMENTS

| | | |
|---|---|---|
| CN | 102018531 A | 4/2011 |
| CN | 102087122 A | 6/2011 |
| CN | 102551792 A | 7/2012 |
| CN | 102783974 A | 11/2012 |
| JP | 2000237986 A | 9/2000 |
| JP | 2004321697 A | 11/2004 |

* cited by examiner

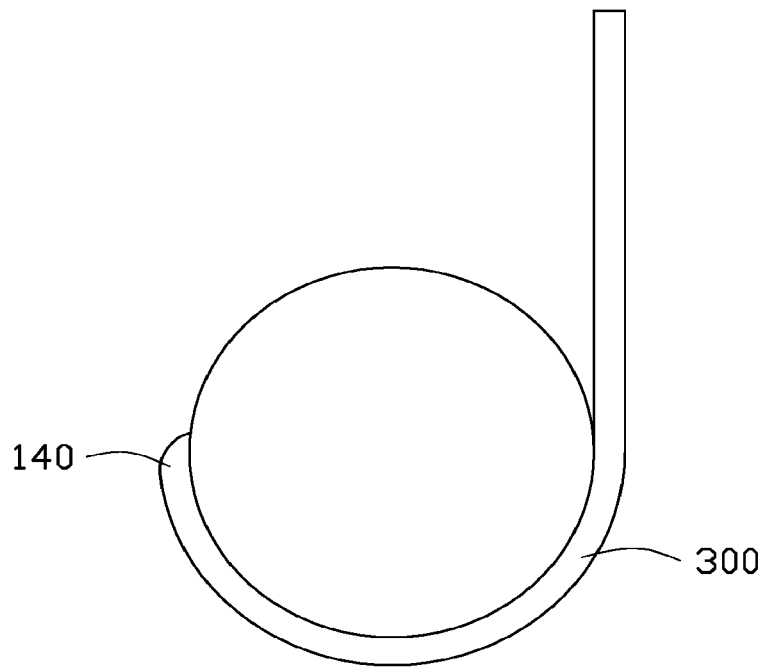
FIG. 10b
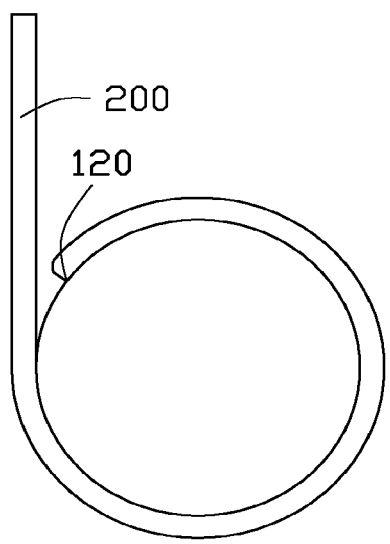 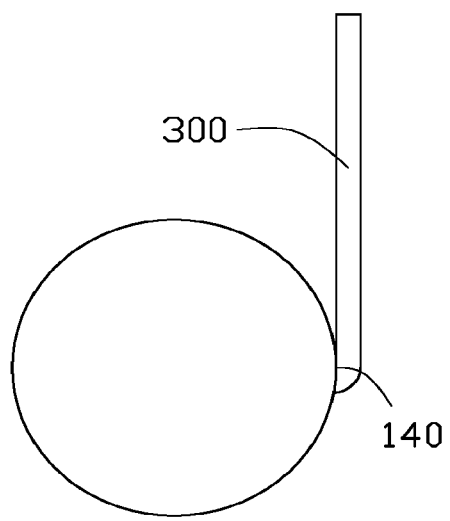
FIG. 11a  FIG. 11b

TENSION TRANSMISSION DEVICE AND THREE-DIMENSIONAL MECHANICAL PROBE USING SAME

CROSS-REFERENCE TO RELATED APPLICATIONS

This application is a continuation under 35 U.S.C. § 120 of international patent application No. PCT/CN2014/074198, filed on Mar. 27, 2014, which claims priority and benefit of Chinese Patent Application No. 201310244524.0, filed on Jun. 19, 2013 in the China Intellectual Property Office, the content of each application is hereby incorporated by reference.

FIELD

The subject matter herein generally relates to medical devices.

BACKGROUND

A type of ultrasonic probe capable of three-dimensional imaging is called a three-dimensional mechanical probe. The three-dimensional mechanical probe usually includes a transducer unit configured to emit ultrasonic waves and receive ultrasonic echoes and a stepper motor used as a driver. The controlled stepper motor drives the transducer unit to swing within a predetermined angle range. The transducer unit emits the ultrasonic waves and receives echoes containing human body tissue information at each swing angle to image the human body tissue at each swing angle of the predetermined angle range, thus a three-dimensional image of the human body tissue is formed.

A three-dimensional mechanical probe can be classified as a three-dimensional body surface mechanical probe and a three-dimensional intracavitary mechanical probe. The three-dimensional intracavitary mechanical probe can be driven via a cable, a cord, or other tension member and/or a bevel gear. The bevel gear transmission demands strict use of a material, a machining, and an assembly. Since the three-dimensional intracavitary mechanical probe requires a small size, such as 25 millimeters diameter for the portion to be inserted into human body, and has a complicated interior structure, it is very difficult to machine and assemble a bevel gear transmission in the three-dimensional intracavitary mechanical probe.

A tension transmission device usually includes two cables fixed to one position on a driving shaft. Thus, a transmission between the driving shaft and a driven shaft can be a linear transmission when the driving shaft rotates within a range of plus or minus 90 degrees. However, an included angle θ is defined between the cables and a vertical direction when the driving shaft rotates beyond the range of plus or minus 90 degrees, and the included angle θ increases when the driving shaft continues to rotate outside the range of plus or minus of 90 degrees, thus the tension transmission between the driving shaft and the driven shaft becomes non-linear, which makes it difficult to manipulate the three-dimensional intracavitary mechanical probe.

SUMMARY

The main technical problem solved by the present disclosure is to provide a tension transmission device and a three-dimensional mechanical probe which can provide linear transmission in a greater rotation range.

A three-dimensional mechanical probe includes a support portion and a probing portion. A bulk of the support portion is greater than a bulk of the probing portion. The support portion includes:

A tension transmission device including a driving shaft, a first tension member, and a second tension member. The driving shaft defines a first fastening point and a second fastening point. The first fastening point and the second fastening point are located at different diametric planes of the driving shaft. The first tension member is connected to the first fastening point and winds around a circumference of the driving shaft. The second tension member is connected to the second fastening point and winds around the circumference of the driving shaft, and;

A first guide pulley set includes a first pulley and a second pulley.

The probing portion includes:

A driven shaft, wherein the first tension member is connected to the driven shaft via the first pulley. The second tension member is connected to the driven shaft via the second pulley.

A tension transmission device includes:

A driving shaft defining a first fastening point and a second fastening point. The first fastening point and the second fastening point are located at different diametric planes of the driving shaft.

A first tension member is connected to the first fastening point and winds around the driving shaft circumferentially.

A second tension member is connected to the second fastening point and winds around the driving shaft circumferentially.

The three-dimensional mechanical probe and the tension transmission device mentioned above include the first tension member and the second tension member. The first tension member is connected to the first fastening point and winds around the driving shaft circumferentially. The second tension member is connected to the second fastening point and winds around the driving shaft circumferentially. The driving shaft rotates to drive the driven shaft via the first guide pulley set and the motion of the first tension member and the second tension member. Rather than the first fastening point and the second fastening point being located at diametrically-opposite points of the driving shaft, the first tension member and the second tension member wind around different diametric planes of the driving shaft. Interference between the tension members is thus avoided. Furthermore, each of the first tension member and the second tension member includes a greater wrapping angle on the driving shaft to make the driving shaft retain linear transmission characteristics within a rotation angle range greater than ninety degrees and allow a greater range in the diameter of the driving shaft. The possible reduction ratios between the driving shaft and the driven shaft also become larger.

BRIEF DESCRIPTION OF THE DRAWINGS

The present disclosure is illustrated by way of embodiments and accompanying drawings.

FIGS. 10a and 10b give schematic views of respective starting positions of the first tension member and the second tension member in accordance with other embodiment.

FIGS. 11a and 11b show positional relationship of the first tension member and the second tension member relative to the driving shaft when the driving shaft of FIGS. 10a and 10b rotates 180° in clockwise direction.

DETAILED DESCRIPTION

The present disclosure is described by way of embodiments and the accompanying drawings. An exemplary embodiment is illustrated. However, the present disclosure can be implemented in many different ways and is not restricted by embodiments described in the present disclosure, the embodiments provided in this disclosure are used for a more comprehensive explanation.

Figure 1:
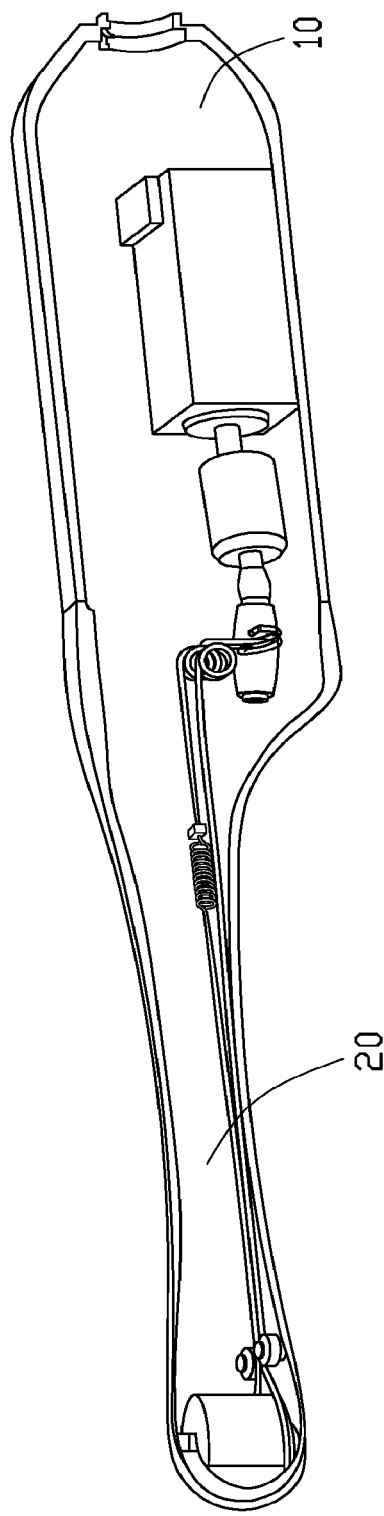
FIG. 1 is a schematic perspective view of a three-dimensional mechanical probe in accordance with one embodiment.
Figure 2:
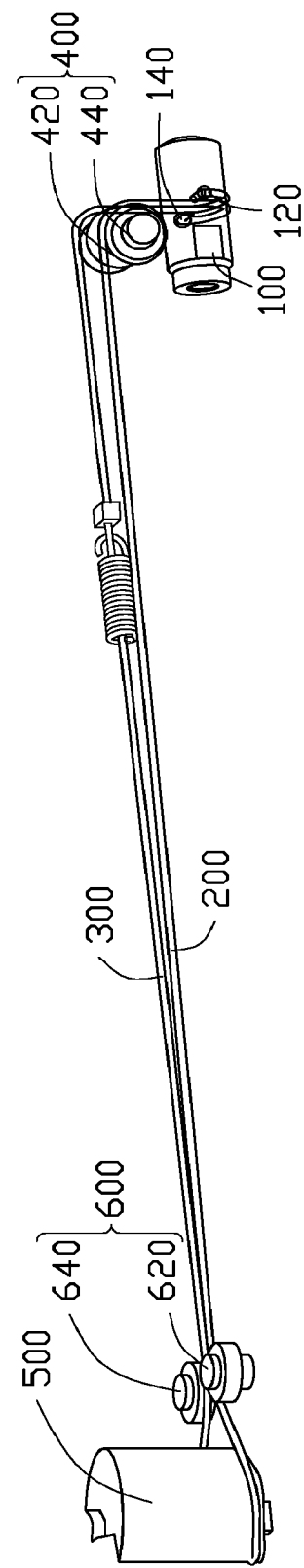
FIG. 2 is a schematic view of a tension transmission device of the three-dimensional mechanical probe in accordance with one embodiment.

Referring to FIGS. 1 and 2, an embodiment of a tension transmission device of a three-dimensional mechanical probe is illustrated. The tension transmission device includes a driving shaft 100, a first tension member 200, and a second tension member 300. The driving shaft 100 defines a first fastening point 120 and a second fastening point 140, and the first fastening point 120 and the second fastening point 140 are located at different diametric planes of the driving shaft 100. The first tension member 200 and the second tension member 300 are thin, long and flexible components which can transmit tension, such as, a cable, a thread, or a cord. The first tension member 200 is connected to the first fastening point 120 and winds around the driving shaft 100. The second tension member 300 is connected to the second fastening point 140 and winds around the driving shaft 100.

Figure 3:
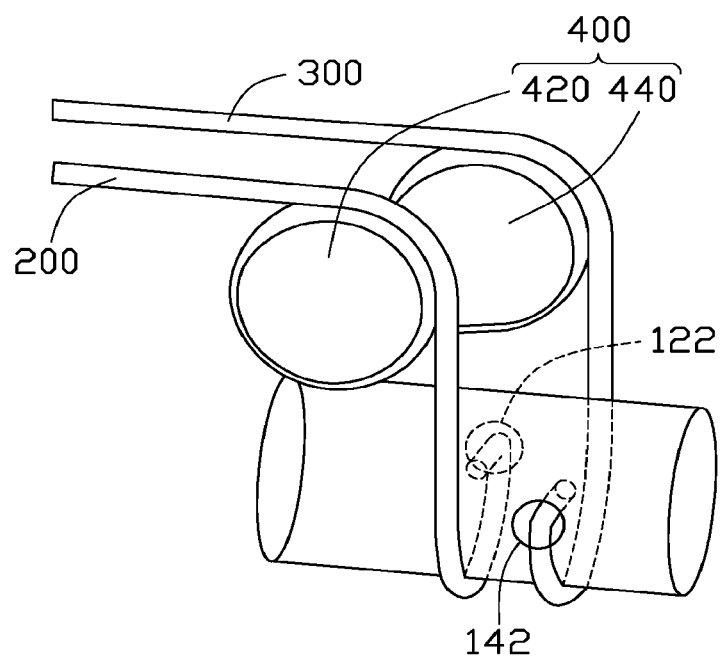
FIG. 3 is a schematic isometric view of a first tension member and a second tension member winding on a driving shaft of the tension transmission device in accordance with one embodiment.

In one embodiment, referring to FIG. 3, the first fastening point 120 defines a first hole 122. The second fastening point MO defines a second hole 142. One end of the first tension member 200 and one end of the second tension member 300 are respectively fastened in the first hole 122 and the second hole 142. Since the first tension member 200 and the second tension member are fastened in the holes 122 and 142, the driving shaft 100 does not need a projection on its outer surface to fasten the first tension member 200 and the second tension member 300. Thus, interference between a tension member and a projection on the outer surface of the driving shaft 100 can be avoided, and a transmission precision can be improved.

In the above-described tension transmission device, because the first tension member 200 and the second tension member 300 are wound around a circumference of the driving shaft 100, and the first fastening point 120 and the second point 140 are located at different diametric planes of the driving shaft 100, the first tension member 200 and the second tension member 300 form tangents with the driving shaft 100 without swinging relative to the driving shaft 100 during a wide angle rotation of the driving shaft 100. Thus, the linear transmission can be achieved. In addition, the first tension member 200 winds around the driving shaft 100 from the first fastening point 120 toward the second fastening point 140 and the second tension member 300 surrounds the second fastening point 140 toward the first fastening point 120. Thus, the first tension member 200 and the second tension member 300 wind around a greater part of the circumference of the driving shaft 100, which makes the driving shaft 100 retain linear transmission characteristics within a wide range of the angular rotation.

Figure 4:
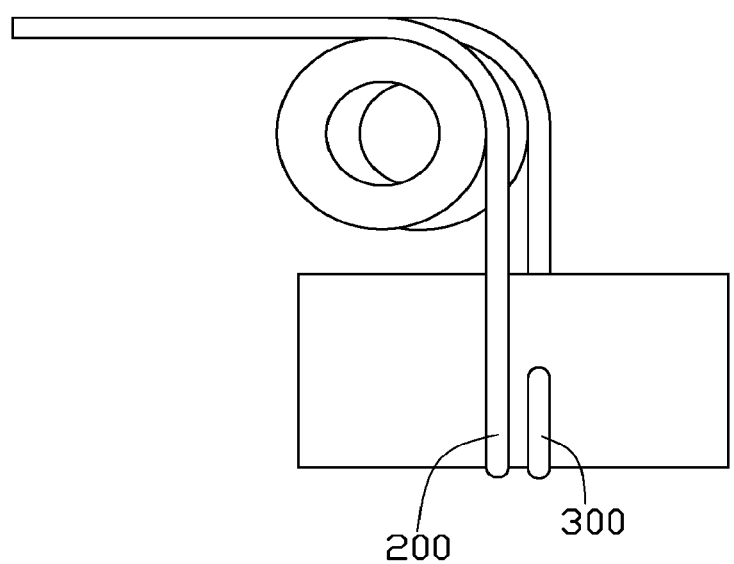
FIG. 4 is a schematic side view of the first tension member and the second tension member winding on the driving shaft of FIG. 3.
Figure 5:
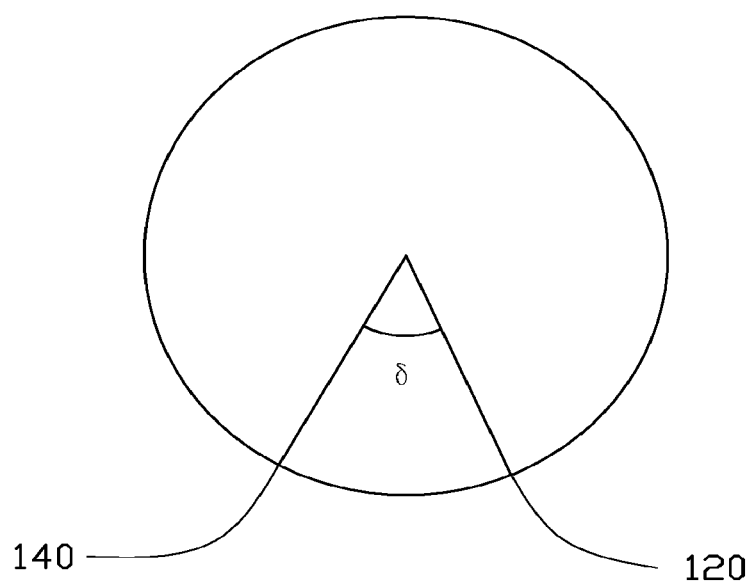
FIG. 5 is a schematic view of a projecting angle defined between extending lines of the first tension member and the second tension member intersecting at a center of the driving shaft in accordance with one embodiment.
Figure 6:
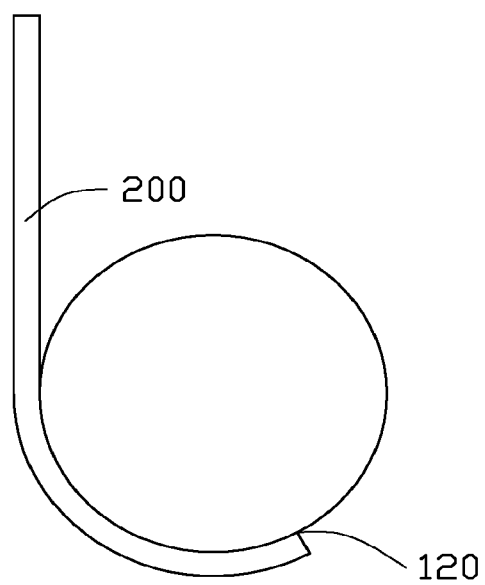
FIGS. 6 and 7 show the respective starting positions of the first tension member and the second tension member in accordance with one embodiment.
Figure 7:
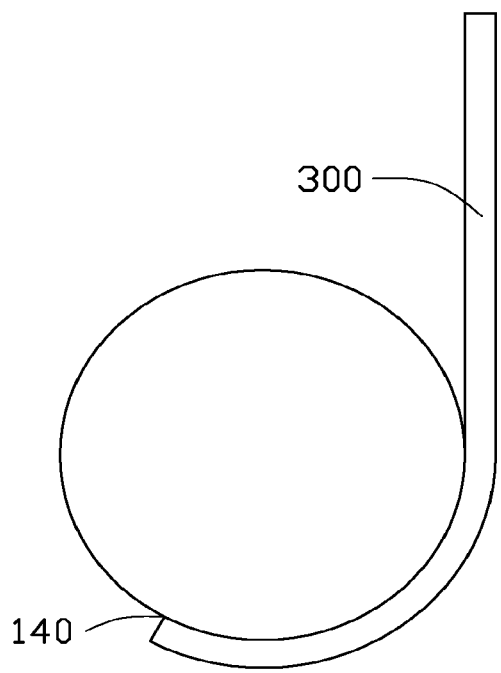

The first tension member 200 and the second tension member 300 wind around the driving shaft 100 in the manner shown in FIG. 3 and FIG. 4. As the first fastening point 120 and the second fastening point 140 are located at different diametric planes, the first tension member 200 and the second tension member 300 accordingly wind around different diametric planes of the driving shaft 100, thereby the first tension member 200 and the second tension members 200 and 300 can operate without mutual interference. Referring to FIG. 5, FIG. 6, and FIG. 7, the first tension member 200 and the second tension member 300 are located at their starting positions on different diametric planes, and define two lines extending from the first fastening point 120 and from the second fastening point 140 to a central line of the driving shaft 100. An included angle d between these two lines can be projected on a cross section of the driving shaft to define a projecting angle δ.

Figure 8A:
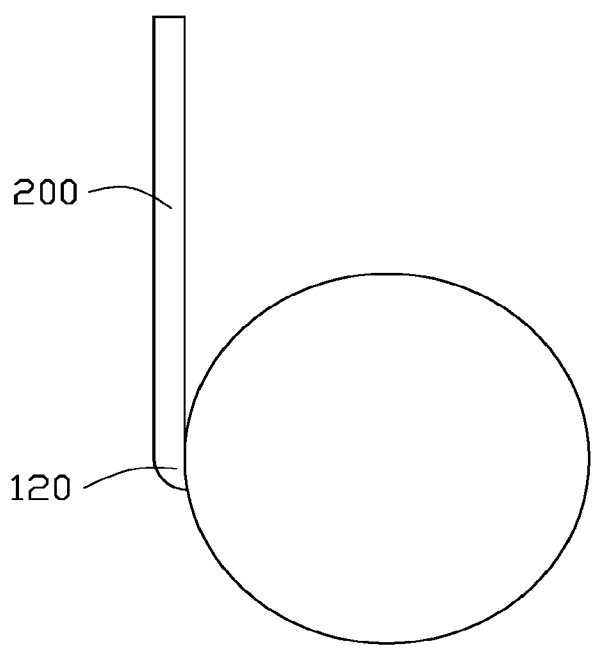
FIGS. 8a and 8b show the positional relationship of the first tension member and the second tension member relative to the driving shaft when the driving shaft of FIGS. 6 and 7 rotates 90°+½ δ in clockwise direction.
Figure 8B:
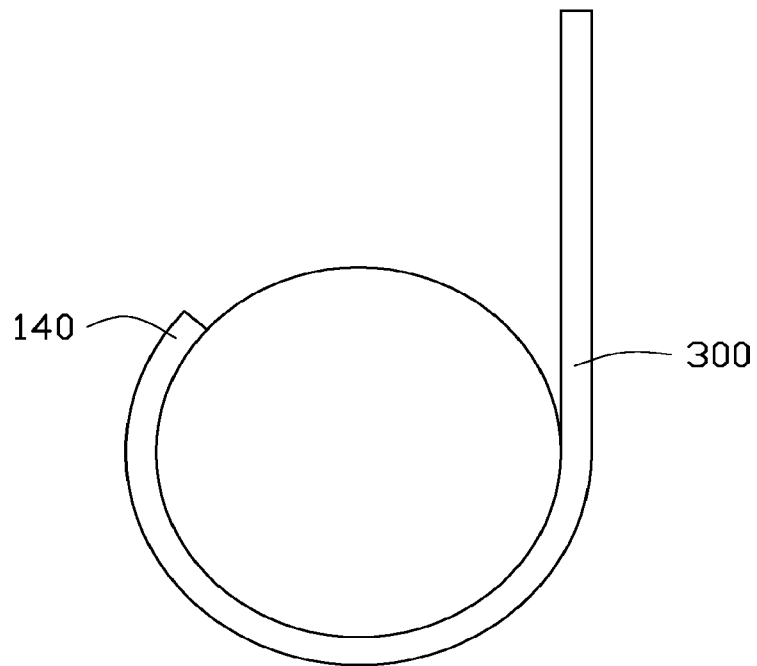
Figure 9A:
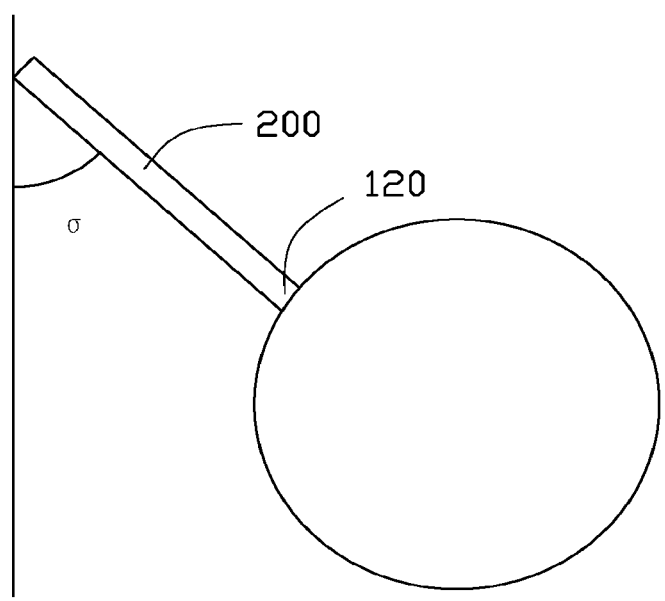
FIGS. 9a and 9b show the positional relationship of the first tension member and the second tension member relative to the driving shaft when the driving shaft of FIGS. 6 and 7 rotates more than 90°+½ δ in clockwise direction.
Figure 9B:
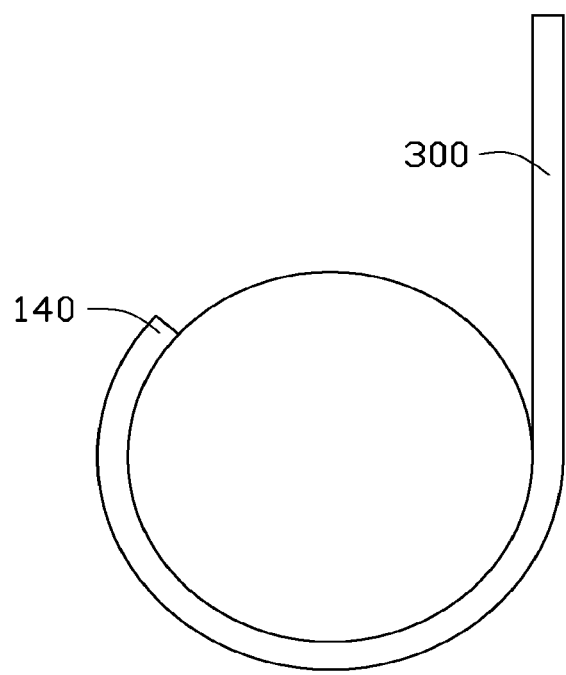

Taking a clockwise rotation of the driving shaft 100 as an example, a wrapping angle of the first tension member 200 on the driving shaft 100 gradually becomes smaller and smaller, and a wrapping angle of the second tension member 300 on the driving shaft 100 becomes greater and greater. When the driving shaft 100 clockwise rotates to an angle 90°+½ δ, as shown in FIGS. 8a and 8b, the first tension member 200 is not wound around the driving shaft 100 and the second tension member 300 is wound around most of the circumference of the driving shaft 100. That is, within the angular rotation range of +(90°+½ δ), the driving shaft 100 can retain linear transmission. Referring to FIG. 9a and FIG. 9b, it is only when the driving shaft 100 goes on rotating that the first tension member 200 will release completely and pass the first fastening point 120, and a part of the first tension member 200 not winding on the driving shaft 100 will define an angle σ with reference to a perpendicular direction, and the transmission become non-linear.

Similarly, when the driving shaft 100 rotates in an anticlockwise direction, the wrapping angle of the first tension member 200 on the driving shaft 100 gradually becomes greater and greater and the wrapping angle of the second tension member 300 on the driving shaft 100 gradually becomes smaller and smaller. When the driving shaft 100 anticlockwise rotates an angle of 90°+½ δ, the second tension member 300 is not wound around the driving shaft 100, and the first tension member 200 is wound around most of the circumference of the driving shaft 100. As the driving shaft 100 goes on rotating, the second tension member 300 will release completely and pass the second fastening point 140, and a part of the second tension member 300 not winding on the driving shaft 100 will define an angle δ with reference to a perpendicular direction. Only then does the transmission becomes non-linear, that is, within the range −(90°+½ δ), the driving shaft 100 retains linear transmission characteristics.

As above, in this embodiment, the driving shaft 100 and its driven shaft 500 can retain linear transmission beyond the usual and conventional rotation range of ±90°, and achieve a rotation range of −(90°+½ δ)~(90°+½ δ).

With the transmission system, the first tension member 200 is connected to the first fastening point 120 and winds around the circumference of the driving shaft 100. The second tension member 300 is connected to the second fastening point 140 and winds around the driving shaft 100 circumferentially. As the first fastening point 120 and the second fastening point 140 are located at different diametric planes, the first tension member 200 and the second tension member 300 wind around the driving shaft 100 at different diametric planes and mutual interference between the first tension member 200 and the second tension member 300 can be avoided. In addition, greater wrapping angles of the first tension member 200 and the second tension member 300 on the driving shaft 100 are achieved, the driving shaft 100 being able to retain linear transmission in a wide range of angular rotation. In this situation, a greater range of the diameter of the driven shaft 500 is possible, and the possible reduction ratio between the driving shaft 100 and the driven shaft 500 also become larger.

Figure 12A:
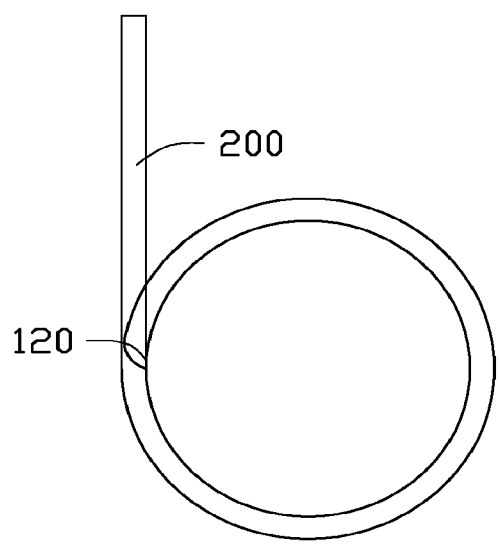
FIGS. 12a and 12b show positional relationship of the first tension member and the second tension member relative to the driving shaft when the driving shaft of FIGS. 10a and 10b rotates more than 180° in clockwise direction.
Figure 12B:
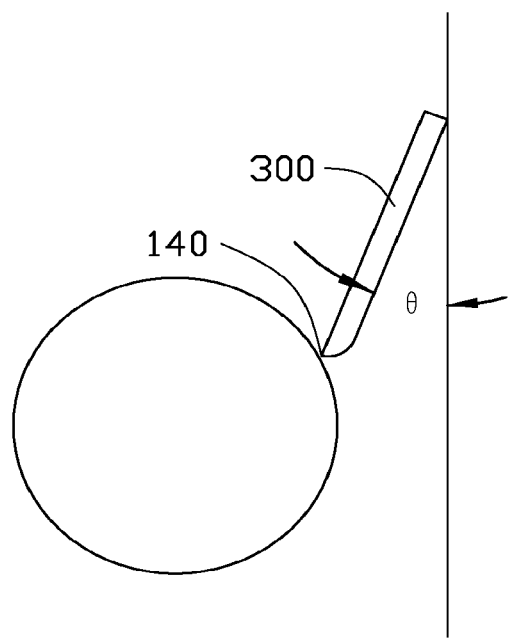

In detail, both of the first fastening point 120 and the second fastening point 140 can be located in a same plane which a central axis of the driving shaft 100 lies on. In this situation, the first tension member 200 and the second tension member 300 define two lines extending from the first fastening point 120 and the second fastening point 140 to a central line of the driving shaft 100, and there is an included angle d between these two lines. The included angle is projected on a cross section of the driving shaft 100 to define a greatest projecting angle δ of 180 degrees. The driving shaft 100 and its driven shaft 500 can retain linear transmission in a rotation range of −180°~±180° Referring to FIG. 10a and FIG. 10b, the first tension member 200 and the second tension member 300 are located at their starting positions, and both wind around half the circumference of the driving shaft 100. FIGS. 11a and 11b illustrate the first tension member 200 winding almost complete around the circumference of the driving shaft 100 and the second tension member 300 being wound only a little on the driving shaft 100 after the driving shaft 100 rotates 180 degrees in anticlockwise direction. When the driving shaft 100 goes on rotating, referring to FIGS. 12a and 12b, the part of the first tension member 200 which winds on the driving shaft 100 will interfere with the other part of the first tension member 200 not winding on the driving shaft 100. Thus, within rotation range of −180°, the driving shaft 100 and the driven shaft 500 retain linear transmission characteristics.

Figure 13A:
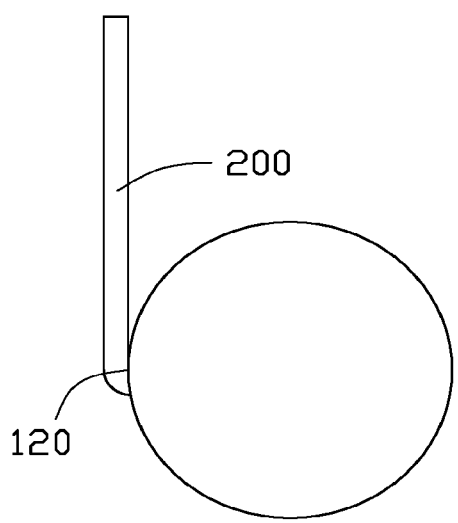
FIGS. 13a and 13b are schematic views of positional relationship of the first tension member and the second tension member relative to the driving shaft when the driving shaft of FIGS. 10a and 10b rotates 180° in anti-clockwise direction.
Figure 13B:
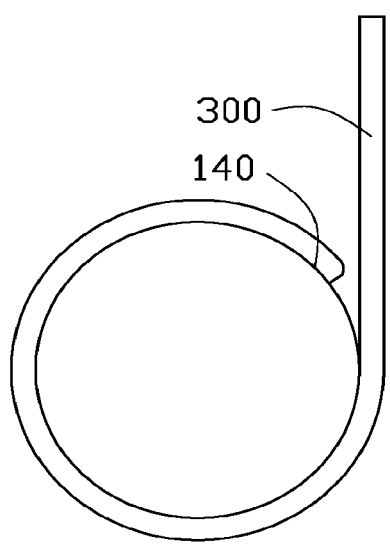

Referring to FIG. 13a and FIG. 13b, within the rotation range of +180 degrees, the driving shaft 100 and the driven shaft 500 can also retain linear transmission.

As above, the driving shaft 100 can retain linear transmission within the rotation range of ±180°, thus a greater range of driven shaft diameters is allowed, for example, the diameter of the driven shaft can be 2-3 times the diameter of the driving shaft 100, and the possible reduction ratio between the driving shaft 100 and the driven shaft 500 also become larger.

Referring to FIGS. 1 and 2, a three-dimensional mechanical probe includes a support portion 10 and a probing portion 20. A bulk of the support portion 10 is greater than that of the probing portion 20. The support portion 10 includes a tension transmission device and a first guide pulley set 400. The probing portion 20 includes a driven shaft 500 and a second guide pulley set 600. The tension transmission device includes a driving shaft 100, a first tension member 200, and a second tension member 300. The driving shaft 100 defines a first fastening point 120 and a second fastening point 140. The first fastening point 120 and the second fastening point 140 are defined at different diametric planes of the driving shaft 100. The first tension member 200 is connected to the first fastening point 120 and winds around the circumference of the driving shaft 100. The second tension member 300 is connected to the second fastening point 140 and winds around the circumference of the driving shaft 100.

In one embodiment, the first guide pulley set 400 includes a first pulley 420 and a second pulley 440. A front part of the first tension member 200, which has passed through the first pulley 420, is perpendicular to a back part of the first tension member 200 which has not yet reached the first pulley 420. A front part of the second tension member 300, which has passed through the second pulley 440, is perpendicular to a back part of the second tension member 300 which has not yet reached the second pulley 440. The first tension member 200 winds around the driven shaft 500 via the first pulley 420. The second tension member 300 winds around the driven shaft 500 via the second pulley 440. A central axis of the driving shaft 100 is perpendicular to a central axis of the driven shaft 500.

The first tension member 200 and the second tension member 300 wind around the driving shaft 100 circumferentially. The first fastening point 120 of the first tension member 200 and the second point 140 of the second tension member 300 are located at different diametric planes of the driving shaft 100, therefore, the first tension member 200 and the second tension member 300 form tangents with the driving shaft 100 without swinging relative to the driving shaft 100 during a wide angle rotation of the deriving shaft 100, thus linear transmission can be achieved. In addition, the first tension member 200 winds around the driving shaft 100 from the first fastening point 120 toward the second fastening point 140 and the second tension member 300 winds around the driving shaft 100 from the second fastening point 140 toward the first fastening point 120, which gives the first tension member 200 and the second tension member 300 a greater wrapping angle on the driving shaft 100, and the driving shaft 100 retains linear transmission characteristic in a great angular rotation range.

The first tension member 200 and the second tension member 300 wind around the driving shaft 100 in a manner illustrated in FIGS. 3 and 4. As the first fastening point 120 and the second fastening point 140 are located at different diametric planes, the first tension member 200 and the second tension member 300 wind around different diametric planes of the driving shaft 100, thereby mutual interference between the first tension member 200 and the second tension member 300 can be avoided. Referring to FIGS. 5, 6, and 7, the first tension member 200 and the second tension member 300 are located at their starting positions on their own diametric planes, and the projecting angle δ is defined between two lines passing through the first fastening point 120 and the second fastening point 140, intersecting at the center axis of the driving shaft 100.

Taking a clockwise rotation of the driving shaft 100 as an example, a wrapping angle of the first tension member 200 on the driving shaft 100 gradually becomes smaller and smaller, and a wrapping angle of the second tension member 300 on the driving shaft 100 gradually becomes greater and greater. When the driving shaft 100 clockwise rotates to an angle 90°+½ δ, as shown in FIGS. 8a and 8b, the first tension member 200 is not wound around the driving shaft 100 and the second tension member 300 is wound around most of the circumference of the driving shaft 100. That is, within the angular rotation range of +(90°+½ δ), the driving shaft 100 can retain linear transmission. Referring to FIG. 9a and FIG. 9b, it is only when the driving shaft 100 goes on rotating that the first tension member 200 will release completely and pass the first fastening point 120, and a part of the first tension member 200 not wound on the driving shaft 100 will define an angle σ as against a perpendicular direction, and the transmission will become non-linear.

Similarly, when the driving shaft 100 rotates in an anti-clockwise direction, the wrapping angle of the first tension member 200 on the driving shaft 100 gradually becomes greater and greater, and the wrapping angle of the second tension member 300 on the driving shaft 200 gradually becomes smaller and smaller. When the driving shaft 100 anticlockwise rotates an angle of 90°+½ δ, the second tension member 300 is not wound around the driving shaft 100, and the first tension member 200 is wound around most of the circumference of the driving shaft 100. As the driving shaft 100 goes on rotating, the second tension member 300 will release completely and pass the second fastening point 140, and a part of the second tension member 300 not wound on the driving shaft 100 will define an angle δ as against a perpendicular direction, and the transmission will become non-linear. That is, within the range −(90°+½ δ), the driving shaft 100 retains linear transmission characteristic.

As above, in this embodiment, the driving shaft 100 and its driven shaft 500 can retain linear transmission beyond the usual and conventional rotation range of ±90°, and achieve a rotation range of −(90°+½ δ) to +(90°+½ δ).

The three-dimensional mechanical probe of this embodiment includes the support portion 10 and the probing portion 20. A bulk of the support portion 10 is greater than that of the probing portion 20, and a transducer unit is installed on the driven shaft 500 of the probing portion 20. In use, the probing portion 20 is inserted into a human body, and the driven shaft 500 is driven to swing within a predetermined angle range by controlling the rotation angle of the driving shaft 100. In each swing angle, the transducer unit can transmit ultrasound waves and receive echoes containing the information of human body tissue, thus the human body tissue at each angle within the predetermined swinging angle range can be imaged and then a three-dimensional image of the human body tissue can be constructed.

In the above tension transmission device of the three-dimensional mechanical probe, the first tension member 200 is connected to the first fastening point 120 and winds around the circumference of the driving shaft 100. The second tension member 300 is connected to the second fastening point 140 and winds around the circumference of the driving shaft 100. When the driving shaft 100 rotates, the driven shaft 500 is driven to rotate via the transmission of the first tension member 200 and the second tension member 300, respectively passing through the first pulley 420 and the second pulley 440. Since the first fastening point 120 and the second fastening point 140 are located at different diametric planes, and the first tension member 200 and the second tension member 300 wind the driving shaft 100 at different diametric planes, the first tension member 200 and the second tension member 300 do not interfere with each other, and the first tension member 200 and the second tension member 300 have a greater wrapping angle on the driving shaft 100, allowing the driving shaft 100 to retain linear transmission in a wide range of the angular rotation. The possible diameter of the driven shaft 500 is increased, and the possible reduction ratio between the driving shaft 100 and the driven shaft 500 also becomes larger.

Moreover, comparing with conventional three-dimensional mechanical probes, the driven shaft 500 of this embodiment can achieve a wide rotation range and the controls of the rotation rate, the rotation angle, and a transmission precision are improved. A driven shaft 500 with a larger diameter allows easier manufacture and assembly of the transducer unit.

Figure 10A:
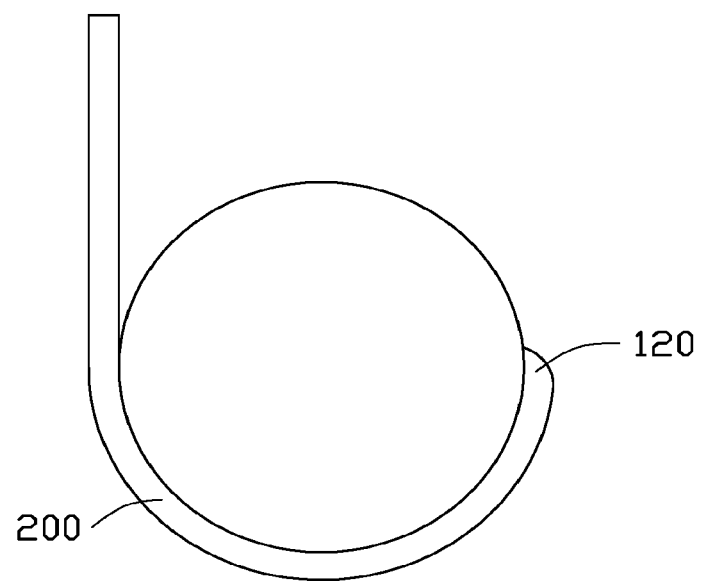

In one embodiment, the first fastening point 120 and the second fastening point 140 are in a same plane with a central axis of the driving shaft 100. In this situation, the greatest projecting angle δ of 180 degrees is defined between two lines respectively passing through the first fastening point 120 and the second fastening point 140 and intersecting at the center axis of the driving shaft 100. The driving shaft 100 and its driven shaft 500 retain linear transmission in a rotation range of −180~+180 degrees. Referring to FIGS. 10a and 10b, the first tension member 200 and the second tension member 300 are located at their own starting positions, and both are wound halfway round the driving shaft 100. FIGS. 11a and 11b illustrate the first tension member 200 almost completely wound on the driving shaft 100 and the second tension member 300 wound on the driving shaft 100 only a little after the driving shaft 100 has rotated 180 degrees in anticlockwise direction. As such, the driving shaft 100 and the driven shaft 500 retain linear transmission within the rotation range of −180 degrees.

Referring to FIGS. 13a and 13b, the driving shaft 100 and the driven shaft 500 can also retain linear transmission characteristics within a rotation range of +180 degrees.

As above, the driving shaft 100 can remain linear transmission within the rotation range of ±180 degree, thus a greater range of the diameter of the driven shaft is allowed, for example, the diameter of the driven shaft can be 2-3 times a diameter of the driving shaft 100, and the possible reduction ratio between the driving shaft 100 and the driven shaft 500 is also larger.

In one embodiment, referring to FIG. 3, the first fastening point 120 defines a first hole 122 and the second fastening point 140 defines a second hole 142. One end of the first tension member 200 and one end of the second tension member 300 are respectively fastened in the first hole 122 and the second hole 142. One or two projections on the outer surface of the driving shaft 100 are not needed to fasten the first tension member 200 and the second tension member 300. Thus, interference between the tension members and the projection on the outer surface of the driving shaft 100 can be avoided, and a transmission precision can be improved.

Figure 14:
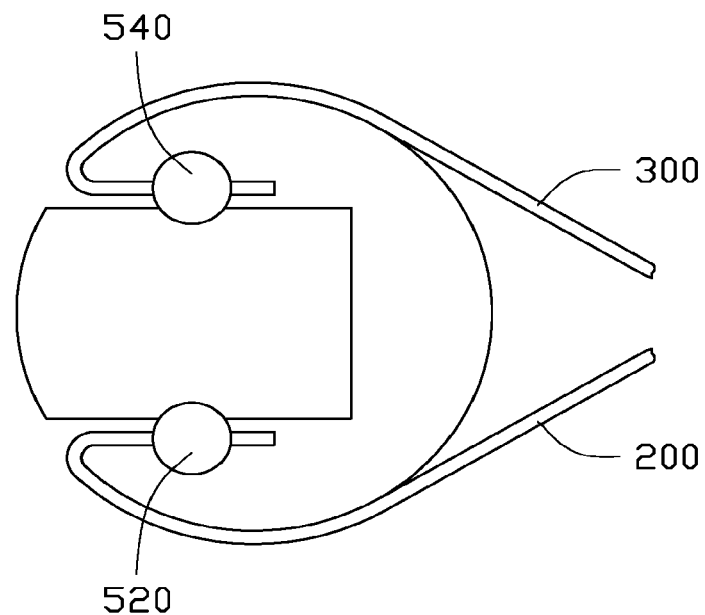
FIG. 14 is a schematic view of a structure of a driven shaft of a three-dimensional mechanical probe in accordance with one embodiment.

In one embodiment, referring to FIG. 14, the driven shaft 500 further defines a third fastening point 520 and a fourth fastening point 540. One end of the first tension member 200 is connected to the third fastening point 520 and one end of the second tension member 300 is connected to the fourth fastening point 540. The first tension member 200 and the second tension member 300 can be fastened to the driven shaft 500 by screws, pins, buckles, or other fasteners. When the first tension member 200 and the second tension member 300 are connected to the driven shaft 500 only by winding, the friction force between the tension members and the driven shaft is weak and can easily allow slipping of the tension members. When the first tension member 200 and the second tension member 300 are fastened to the driven shaft 500, the connection effort therebetween is a combination of the friction force and a tension of the tension members which is strong and relative positions of the tension members and the driven shaft 500 are made more stable. Thus, a transmission efficiency of the tension transmission device is improved.

In this embodiment, the first tension member 200 is connected to the third fastening point 520 and winds around the circumference of the driven shaft 500. The second tension member 300 is connected to fourth fastening point 540 and winds around the circumference of the driven shaft 500. When the driven shaft 500 rotates, the ropes will thus not swing relative to the driven shaft 500 and linear transmission is achieved. Furthermore, the first tension member 200 winds around the driven shaft 500 from the third fastening point 520 towards the fourth fastening point 540, and the second tension member 300 winds around the driven shaft 500 from the fourth fastening point 540 towards the third fastening point 520. Herein, the first tension member 200 and the second tension member 300 are wound around most of the circumference of the driven shaft 500, which provides a greater wrapping angle on the driven shaft 500 and the driven shaft 500 retains linear transmission within a wide range of the angular rotation.

In detail, the driven shaft 500 can define a third hole at the third fastening point 520 and one end of the first tension member 200 is fastened in the third hole. The driven shaft 500 can define a fourth hole at the fourth fastening point 540 and one end of the second tension member 300 is fastened in the fourth hole. The first tension member 200 and the second tension members 300 are fixed in their respective holes, and fasteners are accommodated in the driven shaft 500. The outer surface of the driven shaft 500 being smooth, interference between the tension members and the driven shaft 500 is avoided.

In one embodiment, referring to FIG. 2, the second guide pulley set 600 is arranged near one end of the driven shaft 500. The second guide pulley set 600 includes a third pulley 620 and a fourth pulley 640 opposite to the third pulley 620. A rotating axis of the third pulley 620 and a rotating axis of the fourth pulley 640 are parallel to a central axis of the driven shaft 500. A distance between the first tension member 200 and the second tension member 300 located between the third pulley 620 and the fourth pulley 640 is less than a distance between the first tension member 200 and the second tension member 300 located between the first pulley 420 and the second pulley 440. The former distance is less than a diameter of the driven shaft 500. The first tension member 200 is wound around a side surface of the third pulley 620 near the fourth pulley 640 and connected to the driven shaft 500. The second tension member 300 is wound around a side surface of the fourth pulley 640 near the third pulley 620 and then is connected to the driven shaft 500.

As the distance between the first tension member 200 and the second tension member 300 located between the third pulley 620 and the fourth pulley 640 is less than a diameter of the driven shaft 500, a greater part of the first tension member 200 and of the second tension member 300 is wound on the driven shaft 500. In this way, a wrapping angle of the first tension member 200 and the second tension member 300 on the driven shaft 500 is increased, friction between the first tension member 200, the second tension member 300 and the driven shaft 500 is increased, and the transmission efficiency is improved.

Figure 15:
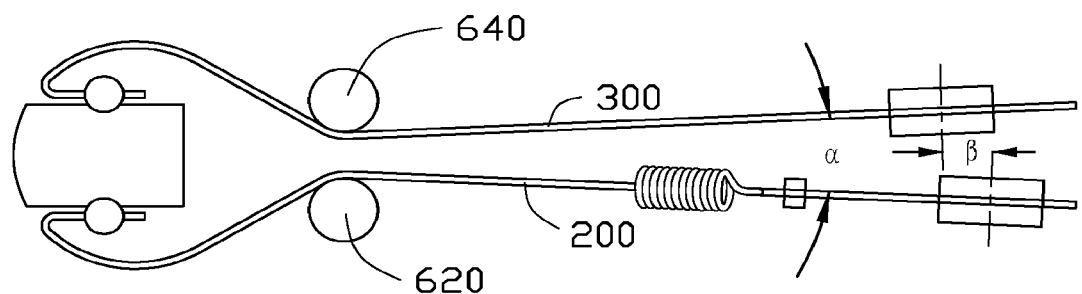
FIG. 15 is a schematic view of a structure of a second guide pulley set of a three-dimensional mechanical probe in accordance with one embodiment.
Figure 16:
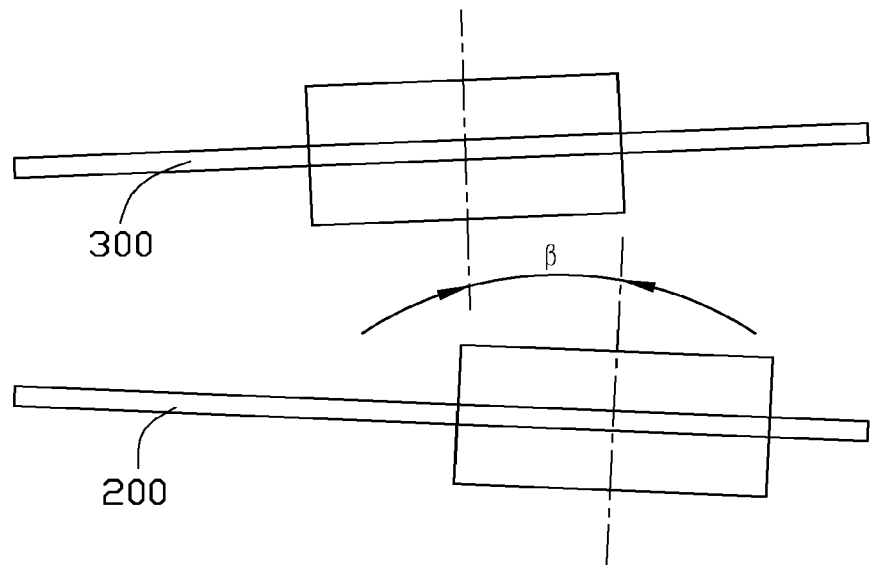
FIG. 16 is a schematic view of positional relationship of different pulleys of a first guide pulley set in accordance with one embodiment.

In detail, as the guide of the third pulley 620 and the fourth pulley 640, referring to FIG. 15, an angle $\alpha$ is defined between the first tension member 200 and the second tension member 300. The magnitude of an angle $\alpha$ depends on a distance between the third pulley 620 and the fourth pulley 640, and also on a distance between the first pulley 420 and the second pulley 440. An angle $\beta$ is defined between a rotating axis of the first pulley 420 and a rotating axis of the second pulley 440. Referring to FIG. 16, when $\alpha=\beta$, a winding direction of the first tension member 200 on the third pulley 620 is in accordance with a rotation direction of the third pulley 620, and a winding direction of the second tension member 300 on the third pulley 640 is in accordance with a rotation direction of the third pulley 640. In this way, linear transmission between the driving shaft 100 and the driven shaft 500 is achieved, a control of transmission becomes easier, and friction between the tension members and the pulley wheels is decreased, thus the transmission efficiency is improved.

Figure 17:
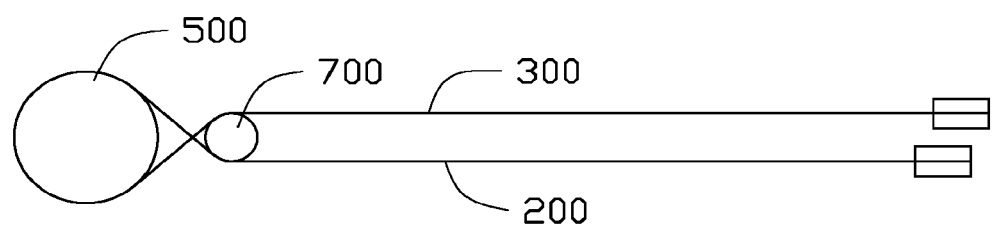
FIG. 17 is a schematic view of a structure of a third guide pulley of a three-dimensional mechanical probe in accordance with one embodiment.

In one embodiment, referring to FIG. 17, a third guide pulley 700 can replace the second guide pulley set 600 at the position near one end of the driven shaft 500. Rotation axis of the third guide pulley 700 is then parallel to a central axis of the driven shaft 500. The first tension member 200 and the second tension member 300 intersect each other after each going through the third guide pulley 700, then winding around the driven shaft 500. The first tension member 200 and the second tension member 300 are positioned on different diametric planes of the third guide pulley 700, which avoids interference between the first tension member 200 and the second tension member 300. With use of the third guide pulley 700, a part of the first tension member 200 and the second tension member 300 wound on the driven shaft 500 becomes longer, and wrapping angles of the first tension member 200 and the second tension member 300 on the driven shaft 500 are increased. Friction between the driven shaft 500 and each of the first tension member 200 and the second tension member 300 is increased, and the transmission efficiency can be improved.

In detail, a winding direction of each of the first tension member 200 and the second tension member 300 on the third guide pulley 700 is in accordance with a rotation direction of the third guide pulley 700, which ensures linear transmission between the third guide pulley 700 and the driving shaft 100. Transmission control becomes more precise, and friction between the tension members and the reversing wheel is decreased, thus transmission efficiency can be improved.

Figure 18:
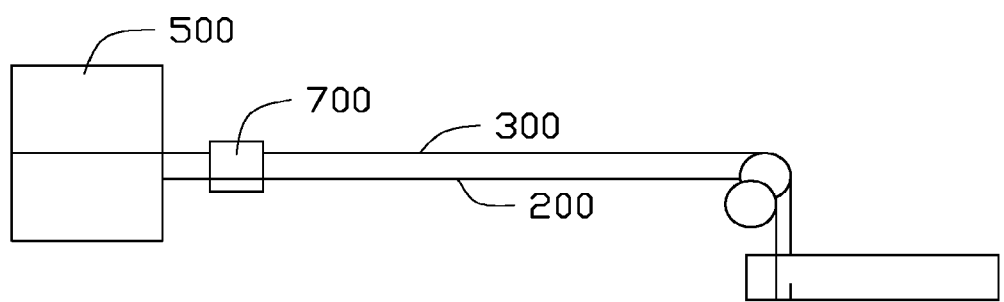
FIG. 18 is a schematic side view of the third guide pulley of FIG. 17.

In one embodiment, referring to FIG. 18, a diameter of the third guide pulley 700 is equal to that of the driving shaft 100. The first tension member 200 and the second tension member 300 remain parallel with each other after going through the first guide pulley set 400. That is, a rotation axis of the first pulley 420 is parallel to that of the second pulley 440. In this way, installation of the first pulley 420 and the second pulley 440 is easier, and further adjustment of the rotation axes of the first pulley 420 and the second pulley 440 is not needed.

The above-described contents are described in embodiments for the present disclosure. The implementation of the present disclosure is not to be limited to these illustrations. For one of ordinary skill in the art, variations and equivalents having the same effects, and application variations, can be made without departing from the spirit of the present disclosure and are to be considered as belonging to the scope of the present disclosure.

The invention claimed is:

1. A three-dimensional mechanical probe comprising:
    a support portion comprising a tension transmission device comprising a driving shaft, a first tension member, and a second tension member, wherein the driving shaft defines a first fastening point and a second fastening point, the first fastening point and the second fastening point are located at different diametric planes of the driving shaft, the first tension member is connected to the first fastening point and winds around a circumference of the driving shaft, and the second tension member is connected to the second fastening point and winds around the circumference of the driving shaft; and
    a probing portion comprising a driven shaft, wherein the first tension member and the second tension member are connected to the driven shaft, wherein the tension transmission device further comprising a first guide pulley set comprising a first pulley and a second pulley, the first tension member is connected to the driven shaft via the first pulley, the second tension member is connected to the driven shaft via the second pulley, a front part of the first tension member which has passed through the first pulley is perpendicular to a back part of the first tension member which has not reached the first pulley, and a front part of the second tension member which has passed through the second pulley is perpendicular to a back part of the second tension member which has not reached the second pulley.

2. The three-dimensional mechanical probe of claim 1, wherein both of the first fastening point and the second fastening point are located in a same plane which a central axis of the driving shaft lies on.

3. The three-dimensional mechanical probe of claim 1, wherein the driving shaft defines a first hole at the first fastening point, one end of the first tension member is fastened in the first hole, the driving shaft defines a second hole at the second fastening point, and one end of the second tension member is fastened in the second hole.

4. The three-dimensional mechanical probe of claim 1, wherein a central axis of the driving shaft is perpendicular to a central axis of the driven shaft.

5. The three-dimensional mechanical probe of claim 1, wherein the first tension member and the second tension member correspondingly winds around the driven shaft circumferentially.

6. The three-dimensional mechanical probe of claim 1, wherein the driven shaft defines a third fastening point and a fourth fastening point, one end of the first tension member is fastened to the third fastening point, and one end of the second tension member is fastened to the fourth fastening point.

7. The three-dimensional mechanical probe of claim 6, wherein the driven shaft defines a third hole at the third fastening point, one end of the first tension member is fastened in the third hole, the driven shaft defines a fourth hole at the fourth fastening point, and one end of the second tension member is fastened in the fourth hole.

8. The three-dimensional mechanical probe of claim 1, wherein the probing portion further comprises a second guide pulley set arranged near one end of the driven shaft, the second guide pulley set comprises a third pulley and a fourth pulley opposite to the third pulley, both of a rotating axis of the third pulley and a rotating axis of the fourth pulley are parallel to a central axis of the driven shaft, the first tension member is wound around a side surface of the third pulley near the fourth pulley, and the second tension member is wound around a side surface of the fourth pulley near the third pulley.

9. The three-dimensional mechanical probe of claim 8, wherein a distance between the first tension member and the second tension member located between the third pulley and the fourth pulley is less than a distance between the first tension member and the second tension member located between the first pulley and the second pulley.

10. The three-dimensional mechanical probe of claim 8, wherein an angle defined between the first tension member and the second tension member which are located between the first guide pulley set and the second guide pulley set is equal to an angle defined between a rotating axis of the first pulley and a rotating axis of the second pulley.

11. The three-dimensional mechanical probe of claim 8, further comprising a third guide pulley set near one end of the driven shaft, wherein a rotating axis of the third pulley is parallel to a central axis of the driven shaft, and the first tension member and the second tension member intersect each other after each going through the third pulley and correspondingly wind around the driven shaft.

12. The three-dimensional mechanical probe of claim 11, wherein the first tension member and the second tension member are positioned on different diametric planes of the third guide pulley.

13. The three-dimensional mechanical probe of claim 11, wherein a diameter of the third guide pulley is equal to a diameter of the driving shaft.

* * * * *